United States Patent
Reardan et al.

(10) Patent No.: US 10,588,947 B2
(45) Date of Patent: *Mar. 17, 2020

(54) ULTRAPURE HYPOALLERGENIC SOLUTIONS OF SACROSIDASE

(71) Applicant: QOL Medical LLC, Vero Beach, FL (US)

(72) Inventors: Dayton T. Reardan, Shorewood, MN (US); Christopher Seekamp, Brookfield, WI (US)

(73) Assignee: QOL Medical LLC, Vero Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,184

(22) Filed: Dec. 15, 2017

(65) Prior Publication Data

US 2018/0193433 A1 Jul. 12, 2018

Related U.S. Application Data

(63) Continuation of application No. 15/270,970, filed on Sep. 20, 2016, now Pat. No. 9,849,161, which is a continuation of application No. 14/828,006, filed on Aug. 17, 2015, now Pat. No. 9,469,847, which is a continuation of application No. 14/175,263, filed on Feb. 7, 2014, now Pat. No. 9,255,261.

(51) Int. Cl.

| *A61K 38/47* | (2006.01) |
| *C12N 9/24* | (2006.01) |
| *C12N 9/26* | (2006.01) |
| *A61K 38/00* | (2006.01) |
| *A61K 38/46* | (2006.01) |
| *A61K 38/43* | (2006.01) |
| *A61P 1/14* | (2006.01) |

(52) U.S. Cl.
CPC ............... *A61K 38/47* (2013.01); *A61P 1/14* (2018.01); *C12N 9/2402* (2013.01); *C12N 9/2405* (2013.01); *C12N 9/2431* (2013.01); *C12Y 302/0101* (2013.01); *C12Y 302/01026* (2013.01); *C12Y 304/22002* (2013.01); *A61K 38/00* (2013.01)

(58) Field of Classification Search
None
See application file for complete search history.

(56) References Cited

U.S. PATENT DOCUMENTS

| 2,786,014 A | 3/1957 | Tullis |
| 4,189,401 A | 2/1980 | Louderback |
| 4,423,600 A | 1/1984 | McKenna |
| 4,688,387 A | 8/1987 | Conaway |
| 5,256,556 A | 10/1993 | Hustedt et al. |
| 9,255,261 B2 | 2/2016 | Reardan et al. |
| 9,469,847 B2 | 10/2016 | Reardan et al. |
| 9,849,161 B2 | 12/2017 | Reardan et al. |
| 2014/0250942 A1 | 9/2014 | Reardan et al. |
| 2015/0225707 A1 | 8/2015 | Reardan et al. |
| 2015/0343032 A1 | 12/2015 | Reardan et al. |
| 2017/0000860 A1 | 1/2017 | Reardan et al. |

FOREIGN PATENT DOCUMENTS

| AU | 2014225740 B2 | 9/2018 |
| EP | 1967583 A1 | 9/2008 |
| EP | 3102228 B1 | 8/2018 |
| MX | 04000698 A | 7/2005 |
| WO | WO-2014138347 A1 | 9/2014 |
| WO | WO-2015120284 A1 | 8/2015 |

OTHER PUBLICATIONS

"U.S. Appl. No. 13/786,956, Response filed Apr. 9, 2018 to Appeal Decision dated Feb. 8, 2018", 10 pgs.
"Australian Application Serial No. 2014225740, Response filed Apr. 23, 2018 to First Examination Report dated Dec. 6, 2017", 9 pgs.
"Canadian Application Serial No. 2,938,733, Office Action dated May 23, 2018", 3 pgs.
"Canadian Application Serial No. 2,938,733, Response filed Jul. 24, 2018 to Office Action dated May 23, 2018", 8 pgs.
U.S. Appl. No. 13/786,956, filed Mar. 6, 2013, Stable Solutions of Sacrosidase.
U.S. Appl. No. 14/175,63, U.S. Pat. No. 9,255,261, filed Feb. 7, 2014, Ultrapure Hypoallergenic Solutions of Sacrosidase.
U.S. Appl. No. 14/828,006, U.S. Pat. No. 9,469,847, filed Aug. 17, 2015, Ultrapure Hypoallergenic Solutions of Sacrosidase.
U.S. Appl. No. 15/270,970, U.S. Pat. No. 9,849,161, filed Sep. 20, 2016, Ultrapure Hypoallergenic Solutions of Sacrosidase.
"2008 > FDA Acts to Avoid Shortage and Strengthen the Safety of Sucraid", [Online]. Retrieved from the Internet: <http://www.fda.gov/NewsEvents/Newsroom/PressAnnouncements/2008/ucm116979.htm>, (Nov. 20, 2008), 3 pgs.
"U.S. Appl. No. 13/786,956, Advisory Action dated Jan. 27, 2015", 2 pgs.
"U.S. Appl. No. 13/786,956, Appeal Brief filed May 13, 2015", 18 pgs.
"U.S. Appl. No. 13/786,956, Decision on Pre-Appeal Brief Request dated Apr. 14, 2015", 2 pgs.
"U.S. Appl. No. 13/786,956, Examiner Interview Summary dated Dec. 2, 2013", 3 pgs.
"U.S. Appl. No. 13/786,956, Examiner's Answer dated Nov. 18, 2015", 11 pgs.
"U.S. Appl. No. 13/786,956, Examiner's Answer dated Dec. 3, 2015", 10 pgs.

(Continued)

*Primary Examiner* — Nghi V Nguyen
(74) *Attorney, Agent, or Firm* — Schwegman Lundberg & Woessner, P.A.

(57) ABSTRACT

The invention provides a method for treating a subject who lacks endogenous sucrase activity by orally administering a solution of sacrosidase in about 1:1 glycerol/water having an enzymatic activity of at least about 7500 IU/mL and a residual papain concentration of less than about 10 ng/ml.

10 Claims, 5 Drawing Sheets

Specification includes a Sequence Listing.

(56) References Cited

OTHER PUBLICATIONS

"U.S. Appl. No. 13/786,956, Final Office Action dated Nov. 3, 2014", 13 pgs.
"U.S. Appl. No. 13/786,956, Non Final Office Action dated Apr. 7, 2014", 10 pgs.
"U.S. Appl. No. 13/786,956, Non Final Office Action dated Nov. 7, 2013", 8 pgs.
"U.S. Appl. No. 13/786,956, Pre-Appeal Brief Request filed Mar. 2, 2015", 5 pgs.
"U.S. Appl. No. 13/786,956, Response filed Jan. 2, 2015 to Final Office Action dated Nov. 3, 2014", 10 pgs.
"U.S. Appl. No. 13/786,956, Response filed Jun. 12, 2014 to Non Final Office Action dated Apr. 7, 2014", 9 pgs.
"U.S. Appl. No. 13/786,956, Response filed Aug. 14, 2013 to Restriction Requirement dated Jul. 29, 2013", 5 pgs.
"U.S. Appl. No. 13/786,956, Response filed Dec. 16, 2013 to Non Final Office Action dated Nov. 7, 2013", 9 pgs.
"U.S. Appl. No. 13/786,956, Restriction Requirement dated Jul. 29, 2013", 6 pgs.
"U.S. Appl. No. 14/175,263, Advisory Action dated May 27, 2015", 4 pgs.
"U.S. Appl. No. 14/175,263, Final Office Action dated Mar. 27, 2015", 8 pgs.
"U.S. Appl. No. 14/175,263, Non Final Office Action dated May 2, 2014", 9 pgs.
"U.S. Appl. No. 14/175,263, Non Final Office Action dated Jul. 27, 2015", 7 pgs.
"U.S. Appl. No. 14/175,263, Non Final Office Action dated Nov. 4, 2014", 14 pgs.
"U.S. Appl. No. 14/175,263, Notice of Allowance dated Nov. 18, 2015", 5 pgs.
"U.S. Appl. No. 14/175,263, Response filed Jan. 29, 2015 to Non Final Office Action dated Nov. 4, 2014", 9 pgs.
"U.S. Appl. No. 14/175,263, Response filed Apr. 23, 2015 to Final Office Action dated Mar. 27, 2015", 8 pgs.
"U.S. Appl. No. 14/175,263, Response filed Jun. 27, 2014 to Non Final Office Action dated May 2, 2014", 13 pgs.
"U.S. Appl. No. 14/175,263, Response filed Aug. 17, 2015 to Non Final Office Action dated Jul. 27, 2015", 5 pgs.
"U.S. Appl. No. 14/828,006, Corrected Notice of Allowance dated Sep. 15, 2016", 2 pgs.
"U.S. Appl. No. 14/828,006, Notice of Allowance dated Jun. 7, 2016", 9 pgs.
"U.S. Appl. No. 14/828,006, Non Final Office Action dated Dec. 21, 2015", 13 pgs.
"U.S. Appl. No. 15/270,970, Non Final Office Action dated Feb. 16, 2017", 14 pgs.
"U.S. Appl. No. 15/270,970, Notice of Allowance dated Aug. 18, 2017", 8 pgs.
"U.S. Appl. No. 15/270,970, Response filed May 16, 2017 to Non Final Office Action dated Feb. 16, 2017", 9 pgs.
"U.S. Appl. No. PCT/US2014/021050, International Preliminary Report on Patentability dated Sep. 17, 2015", 9 pgs.
"Australian Application Serial No. 2014225740, First Examination Report dated Dec. 6, 2017", 4 pgs.
"Canadian Application Serial No. 2,938,733, Office Action dated Jun. 28, 2017", w/ English Translation, 4 pgs.
"European Application Serial No. 14717895.8, Communication Pursuant to Article 94(3) EPC dated Aug. 16, 2016", 5 pgs.
"European Application Serial No. 14717895.8, Response filed Dec. 14, 2016 to Communication Pursuant to Article 94(3) EPC dated Aug. 16, 2016", 10 pgs.
"European Application Serial No. 14717895.8, Summons to Attend Oral Proceedings dated Jan. 11, 2017", 3 pgs.
"European Patent Application No. 15706592.1, Response filed Apr. 12, 2017 to Communication pursuant to Rules 161(1) and 162 EPC", 13 pgs.
"FDA Warns Companies to Stop Marketing Unapproved Ophthalmic Balanced Salt Solution Drug Products and Topical Drug Products Containing Papain", FDA News Release, [Online]. Retrieved from the Internet: <URL: http://www.fda.gov/NewsEvents/Newsroom/PressAnnouncements/2008/ucm116956.htm>, (Sep. 23, 2008), 3 pgs.
"Glycerol", WebMD, [Online]. Retrieved from the Internet: <URL: http://www.webmd.com/vitamins-supplements/ingredientmono-4-Glycerol.aspx?activeIngredientId=4&activeIngredientName=Glycerol&source=1>, (Accessed Mar. 25, 2014), 3 pgs.
"International Application Serial No. PCT/US2014/021050, International Search Report dated Jun. 16, 2014", 4 pgs.
"International Application Serial No. PCT/US2014/021050, Written Opinion dated Jun. 16, 2014", 7 pgs.
"International Application Serial No. PCT/US2015/014837, International Preliminary Report on Patentability dated Aug. 18, 2016", 8 pgs.
"International Application Serial No. PCT/US2015/014837, International Search Report dated May 19, 2015", 4 pgs.
"International Application Serial No. PCT/US2015/014837, Written Opinion dated May 19, 2015", 7 pgs.
"Opinion: Ex parte Sobin, Celmer, and Koe", 1963 Pat. App. Lexis 5; 139 U.S.P.Q. (BNA) 528, Board of Patent Interferences, Jan. 31, 1962, (Jan. 31, 1962), 2 pgs.
"Orphan Medical announced the commercial availability of SUCRAID (Sacrosidase) oral solution", PR Newswire, (Jul. 17, 1998), 3 pgs.
"Proposed REMS for Sucraid Oral Solution", NDA 20-772 Sucraid (sacrosidase) Oral Solution, 8,500 IU/ml, Enzyme replacement supplement for Treatment of CSID, (2008), 9 pgs.
"Revised Labeling to be Implemented with Next Lot of Sucraid Oral Solution Manufactured at PPI", QOL Medical LLC; Sucraid Oral Solution, NDS 20-722S007 Amendment 11, (Nov. 17, 2008), 2 pgs.
"Sacrosidase", [Online] Retrieved From Internet: <http://www.drugs.com/mtm/sacrosidase.html>, (Accessed Oct. 23, 2013), 4 pgs.
"Sucraid", rxlist, [Online]. Retrieved from the Internet: <URL: http://www.rxlist.com/sucraid-drug.htm>, (Accessed Oct. 23, 2013), 6 pgs.
"Sucraid", CSID Parent Support Group, (2004), 7 pgs.
"Sucraid—sacrosidase solution", QOL Medical, LLC, XP002724941, (May 2010).
"Sucraid Official FDA information, side effects and uses", [Online]. Retrieved from the Internet: <http://web.archive.org/web/20130221135524/http://www.drugs.com/pro/sucraid.html>, (Feb. 21, 2013).
Benau, D., et al., "Endogenous inhibitors of cyclic adenosine 3',5'-monophosphate-phosphodiesterase in rat epididymis", US National Library of Medicine (NLM), Database accession No. NLM3028516, (Nov. 1986)
Bradbury, S. L., et al., "Glycerol as Enzyme-Stablizing Agent: Effects on Aldehyde Dehydrogenase", Proc. Natl. Acad. Sci. USA, 69(9), (1972), 2373-2376.
Burger, M., et al., "Some Observations on the Form and Location of Invertase in the Yeast Cell", Biochem J. (1961) 78, 504, (1961), 504-511.
Carpenter, J. F., et al., "The Mechanism of Cryoprotection of Proteins by Solutes", Cryobiology, 25, (1988), 244-255.
Chang, B. S., et al., "Surface-induced denaturation of proteins during freezing and its inhibition by surfactants", J. Pharm. Sci., 85(12), (1996), 1325-1330.
Jameel, F., et al., "Investigation of physicochemical changes to L-asparaginase during freeze-thaw cycling", J. Pharm. Pharmacol., 49(5), (1997), 472-477.
Kidby, D. K., et al., "Invertase and Disulphide Bridges in the Yeast Wall", Journal of General Microbiology, 61, (1970), 327-333.
Koertge, T. E, et al., "Characterization of the soluble immune complex (EIC) of the amplified enzyme-linked immunosorbent assay (a-ELISA) and an evaluation of this assay for quantitation by reaction stoichiometry", US National Library of Medicine (NLM), Database accession no. NLM3833874, (1985).
Lampen, J. O., "External enzymes of yeast: their nature and formation", Antonie van Leeuwenhoek 34 (1968) 1-18, (1968), 1-18.

(56) References Cited

OTHER PUBLICATIONS

McIntosh, Kylie A., et al., "Analytical methods and stability assessment of liquid yeast derived sucrase", Journal of Pharmaceutical and Biomedical Analysis, 17 (1998), 1037-1045, (Jan. 2, 1998), 1037-1045.

Myrback, Karl, "Studies on Yeast Invertase. Soluble and Insoluble Invertase (Saccharase) of Baker's Yeast", Aiwhives of Biochemistry and Biophysics 69, (1957), 138-148.

Nascimento, Catia, et al., "Polyol Additives Modulate the In Vitro Stability and Activity of Recombinant Human Phenylalanine Hydroxylase", Applied Biochemistry And Biotechnology, vol. 162, No. 1, (Sep. 2010), 192-207.

Nath, Nidhi, et al., "Improving Protein Array Performance Focus on Washing and Storage Conditions", Journal of Proteome Research, vol. 7, No. 10, (Oct. 1, 2008), 4475-4482.

Nowak, J., et al., "The yeast aminopeptidase Y", US National Library of Medicine (NLM), Database accession No. NLM3042113, Bethesda, MD, US, (Feb. 1988).

Payne, R. C, et al., "Uridine kinase from Ehrlich ascites carcinoma. Purification and properties of homogeneous enzyme", The Journal of Biological Chemistry, vol. 260, No. 18, (Aug. 25, 1985), 10242-10247.

Pikal-Cleland, K. A., et al., "Protein Denaturation during Freezing and Thawing in Phosphate Buffer Systems: Monomeric and TetramericB-Galactosidase", Archives of Biochemistry and Biophysics, 384(2), (2000), 398-406.

Rome, L. H, et al., "Properties of a partially-purified preparation of the prostaglandin-forming oxygenase from sheep vesicular gland", Prostaglandins, vol. 10, No. 5, (Nov. 1, 1975), 813-824.

Sanders, Catherine, "Sucraid (Sacrosidase)", Ventura County Health Care Plan, (Jan. 28, 2014), 2 pgs.

Simpson, R. J., "Stabilization of Proteins for Storage", Cold Spring Harb. Protoc., vol. 2010, Issue 5, (2010), 1-14.

Taussig, Ronald, et al., "Nucelotide sequence of the yeast SUC2 gene for invertase", Nucleic Acids Research, vol. 11, No. 6 (1983), (Jan. 3, 1983), 12 pgs.

Vagenende, Vincent, et al., "Mechanisms of Protein Stabilization and Prevention of Protein Aggregation by Glycerol", Biochemistry, vol. 48, No. 46, (2009), 11084-11096.

Wiseman, A., et al., "Assay-Increment and Solubilisation of a-Glucosidase and Invertase in Disruption of Brewers' Yeast", J. Appl. Chem. Biotechnol. 21, (1971), 26-28.

Zarate, V., et al., "Characterization of the heterologous invertase produced by Schizosaccharomyces pombe from the SUC2 gene of *Saccharomyces cerevisiae*", Journal of Applied Bacteriology, 1996, 80, (1996), 45-52.

Zech, M., et al., "Invertase from *Saccharomyces cerevisiae*: Reversable inactivation by components of industrial molasses media", Enzyme and Microbial Technology,17, (1995), 41-46.

"U.S. Appl. No. 13/786,956, Appeal Decision dated Feb. 8, 2018", 14 pgs.

"Canadian Application Serial No. 2,938,733, Response filed Dec. 21, 2017 to Office Action dated Jun. 28, 2017", 9 pgs.

"Canadian Application Serial No. 2,938,733, Response filed May 14, 2019 to Office Action dated Jan. 9, 2019", 12 pages.

"Canadian Application Serial No. 2,938,733, Office Action dated Jan. 9, 2019", 4 pgs.

"European Application Serial No. 18175578.6, Extended European Search Report dated Nov. 16, 2018", 5 pgs.

"European Application Serial No. 18175578.6, Response filed Feb. 8, 2019 to Extended European Search Report dated Nov. 16, 2018", 36 pgs.

Figure 1 Flow Diagram of the Manufacturing Process

| Step / Equipment | Materials | Process Control | Outputs |
|---|---|---|---|
| 1. Digestion of yeast in (1000 gal reactor) | • deionized water (filtered)<br>• yeast<br>• sodium hydroxide, 25% solution<br>• papain (100 TU/mg)<br>• hydrogen peroxide | 30° - 34°C<br>pH = 7 ± 0.1<br>Hold 17.5 to 22 hours | Mixture with cell debris and dissolved proteins. |
| 2. Acidification of digest | • phosphoric acid, 85%<br>• diatomaceous earth | 23° - 26°C<br>pH = 4.0 ± 0.1 | Mixture with cell debris and dissolved proteins. Papain inactivated. |
| 3. Removal of Cell Debris (Sparkler filter) | • deionized water (filtered)<br>• filter paper | 20° - 25°C | Protein solution. |
| 4. Decolorization of filtrate | • activated carbon<br>• hydrogen peroxide solution<br>• aluminum sulfate<br>• diatomaceous earth<br>• filter paper | 23° - 27 °C<br>Hold 30-60 minutes. | Mixture with carbon, aluminum hydroxide floccules, and dissolved proteins. |
| 5. Removal of Solids (Sparkler filter) | | No more than a trace amount of carbon remaining in liquid. Filter in-line through a 0.2 micron filter. | Clarified protein solution. |
| 6. Concentration via Ultrafiltration (Ultrafiltration Rig) | • 40 kDa Molecular Weight Cut-Off polyethersulfone filter membrane | 22°-28°C; sufficient volume reduction for batch to fit in UF rig. | Concentrated Sacrosidase solution (~250 L) |
| 7. Diafiltration followed by concentration (Ultrafiltration Rig) | • deionized water (filtered)<br>• sodium citrate<br>• citric acid<br>• sodium hydroxide, 25% | pH=4.6 ± 0.1<br>Target sucrase activity of ≥ 22,000 IU/mL. | Concentrated, ultra-pure Sacrosidase solution. Papain concentration substantially reduced. |
| 8. Adjust pH (1000 L Tote w/ Recirculating Pump) | • phosphoric acid, 85% or<br>• sodium hydroxide, 25% | pH~4.2 ± 0.1 | Concentrated Sacrosidase with optimal pH |
| 9. Blending with Glycerin | • glycerin | Target sucrase assay value of ≥ 10,000 IU/mL and a glycerin content of 45 to 54% by weight. | Concentrated Sacrosidase solution, containing glycerin. |
| 10. Filtration into HDPE Drums | • Filter in-line through two 0.2 micron filters in series. | | Filtered, concentrated Sacrosidase solution, containing glycerin. |

*FIG. 1*

```
  1 SMTNETSDRP LVHFTFNKGW MNDPNGLWYD EKDAKWHLYF QYNPNDTVWG
 51 TPLFWGHATS DDLTNWEDQP IAIAPKRNDS GAFSGSMVVD YNNTSGFFND
101 TIDPRQRCVA IWTYNTPESE EQYISYSLDG GYTFTEYQKN PVLAANSTQF
151 RDPKVFWYEP SQKWIMTAAK SQDYKIEIYS SDDLKSWKLE SAFANEGFLG
201 YQYECPGLIE VPTEQDPSKS YWVMFISINP GAPAGGSFNQ YFVGSFNGTH
251 FEAFDNQSRV VDFGKDYYAL QTFFNTDFTY GSALGIAWAS NWEYSAFVPT
301 NPWRSSMSLV RKFSLNTEYQ ANPETELINL KAEPILNISN AGPWSRFATN
351 TTLTKANSYN VDLSNSTGTL EFELVYAVNT TQTISKSVFA DLSLWFKGLE
401 DPEEYLRMGF EVSASSFFLD RGNSKVKFVK ENPYFTNRMS VNNQPFKSEN
451 DLSYYKVYGL LDQNILELYF NDGDVVSTNT YFMTTGNALG SVNMTTGVDN
501 LFYIDKFQVR EVK
```

The amino acid composition for sacrosidase is shown below.

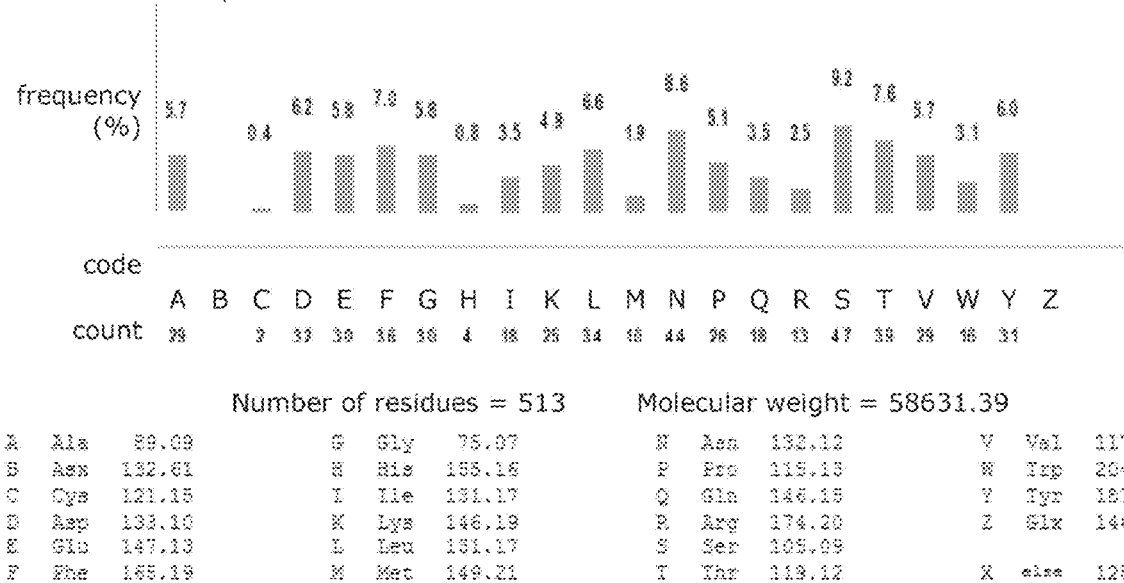

Number of residues = 513    Molecular weight = 58631.39

The molecular formula for Sacrosidase, based on the amino acid composition, is $C_{2662}H_{4909}N_{663}O_{1329}S_{12}$.

FIG. 5

SEQUENCE LISTING

```
<160> NUMBER OF SEQ ID NOS: 1

<210> SEQ ID NO 1
<211> LENGTH: 513
<212> TYPE: PRT
<213> ORGANISM: Homo sapiens

<400> SEQUENCE: 1

Ser Met Thr Asn Glu Thr Ser Asp Arg Pro Leu Val His Phe Thr Pro
1               5                   10                  15

Asn Lys Gly Trp Met Asn Asp Pro Asn Gly Leu Trp Tyr Asp Glu Lys
            20                  25                  30

Asp Ala Lys Trp His Leu Tyr Phe Gln Tyr Asn Pro Asn Asp Thr Val
        35                  40                  45

Trp Gly Thr Pro Leu Phe Trp Gly His Ala Thr Ser Asp Asp Leu Thr
    50                  55                  60

Asn Trp Glu Asp Gln Pro Ile Ala Ile Ala Pro Lys Arg Asn Asp Ser
65                  70                  75                  80

Gly Ala Phe Ser Gly Ser Met Val Val Asp Tyr Asn Asn Thr Ser Gly
                85                  90                  95

Phe Phe Asn Asp Thr Ile Asp Pro Arg Gln Arg Cys Val Ala Ile Trp
            100                 105                 110

Thr Tyr Asn Thr Pro Glu Ser Glu Glu Gln Tyr Ile Ser Tyr Ser Leu
        115                 120                 125

Asp Gly Gly Tyr Thr Phe Thr Glu Tyr Gln Lys Asn Pro Val Leu Ala
    130                 135                 140

Ala Asn Ser Thr Gln Phe Arg Asp Pro Lys Val Phe Trp Tyr Glu Pro
145                 150                 155                 160

Ser Gln Lys Trp Ile Met Thr Ala Ala Lys Ser Gln Asp Tyr Lys Ile
                165                 170                 175

Glu Ile Tyr Ser Ser Asp Asp Leu Lys Ser Trp Lys Leu Glu Ser Ala
            180                 185                 190

Phe Ala Asn Glu Gly Phe Leu Gly Tyr Gln Tyr Glu Cys Pro Gly Leu
        195                 200                 205

Ile Glu Val Pro Thr Glu Gln Asp Pro Ser Lys Ser Tyr Trp Val Met
    210                 215                 220

Phe Ile Ser Ile Asn Pro Gly Ala Pro Ala Gly Gly Ser Phe Asn Gln
225                 230                 235                 240

Tyr Phe Val Gly Ser Phe Asn Gly Thr His Phe Glu Ala Phe Asp Asn
                245                 250                 255

Gln Ser Arg Val Val Asp Phe Gly Lys Asp Tyr Tyr Ala Leu Gln Thr
            260                 265                 270

Phe Phe Asn Thr Asp Pro Thr Tyr Gly Ser Ala Leu Gly Ile Ala Trp
        275                 280                 285

Ala Ser Asn Trp Glu Tyr Ser Ala Phe Val Pro Thr Asn Pro Trp Arg
    290                 295                 300

Ser Ser Met Ser Leu Val Arg Lys Phe Ser Leu Asn Thr Glu Tyr Gln
```

```
305                 310                 315                 320
Ala Asn Pro Glu Thr Glu Leu Ile Asn Leu Lys Ala Glu Pro Ile Leu
                325                 330                 335

Asn Ile Ser Asn Ala Gly Pro Trp Ser Arg Phe Ala Thr Asn Thr Thr
                340                 345                 350

Leu Thr Lys Ala Asn Ser Tyr Asn Val Asp Leu Ser Asn Ser Thr Gly
            355                 360                 365

Thr Leu Glu Phe Glu Leu Val Tyr Ala Val Asn Thr Thr Gln Thr Ile
        370                 375                 380

Ser Lys Ser Val Phe Ala Asp Leu Ser Leu Trp Phe Lys Gly Leu Glu
385                 390                 395                 400

Asp Pro Glu Glu Tyr Leu Arg Met Gly Phe Glu Val Ser Ala Ser Ser
                405                 410                 415

Phe Phe Leu Asp Arg Gly Asn Ser Lys Val Lys Phe Val Lys Glu Asn
                420                 425                 430

Pro Tyr Phe Thr Asn Arg Met Ser Val Asn Asn Gln Pro Phe Lys Ser
            435                 440                 445

Glu Asn Asp Leu Ser Tyr Tyr Lys Val Tyr Gly Leu Leu Asp Gln Asn
    450                 455                 460

Ile Leu Glu Leu Tyr Phe Asn Asp Gly Asp Val Val Ser Thr Asn Thr
465                 470                 475                 480

Tyr Phe Met Thr Thr Gly Asn Ala Leu Gly Ser Val Asn Met Thr Thr
                485                 490                 495

Gly Val Asp Asn Leu Phe Tyr Ile Asp Lys Phe Gln Val Arg Glu Val
                500                 505                 510

Lys
```

ULTRAPURE HYPOALLERGENIC SOLUTIONS OF SACROSIDASE

CLAIM OF PRIORITY

This application is a continuation and claims the benefit of priority of U.S. patent application Ser. No. 15/270,970, filed on Sep. 20, 2016, which is a continuation and claims the benefit of priority to U.S. patent application Ser. No. 14/828,006, filed on Aug. 17, 2015 which claims the benefit of priority of U.S. patent application Ser. No. 14/175,263, filed on Feb. 7, 2014, which are incorporated by reference herein in their entirety.

BACKGROUND OF THE INVENTION

Congenital sucrase-isomaltase deficiency (CSID) is a chronic, autosomal recessive, inherited, phenotypically heterogenous disease with variable enzyme activity. CSID is usually characterized by a subject having complete or almost complete lack of endogenous human sucrase activity, along with a very marked reduction in isomaltase activity, a moderate decrease in maltase activity, and the subject can have normal or abnormal lactase levels.

The human enzyme sucrase-isomaltase is naturally produced in the brush border of the small intestine, primarily the distal duodenum and jejunum. The natural human enzyme hydrolyzes the disaccharide sucrose into its component monosaccharides, glucose and fructose. Isomaltase breaks down disaccharides from starch into simple sugars.

In the absence of endogenous human sucrase-isomaltase enzyme, as in CSID, sucrose is not metabolized. Unhydrolyzed sucrose and starch are not absorbed from the intestine and their presence in the intestinal lumen leads to osmotic retention of water. This may result in loose stools or diarrhea. Unabsorbed sucrose in the colon is fermented by bacterial flora to produce increased amounts of hydrogen, methane and water. As a consequence, excessive gas, bloating, abdominal cramps, nausea, vomiting, and explosive diarrhea may occur. Chronic malabsorption of disaccharides may result in malnutrition. Undiagnosed/untreated CSID patients often fail to thrive and fall behind in their expected growth and development curves. Prior to the FDA approval of the commercial replacement product Sucraid® (sacrosidase) Oral Solution, the treatment of CSID has required the continued use of a strict sucrose-free diet with limited success in disease management.

CSID is currently treated by the oral administration, with meals, of a glycerol-water (1:1 w/w) solution of sacrosidase, which provides the enzyme replacement therapy for CSID. This solution is commercially provided as Sucraid® (sacrosidase) Oral Solution distributed by QOL Medical LLC. Each milliliter (mL) of Sucraid® contains 8500 International Units (I.U.) of the enzyme sacrosidase, the active ingredient. The chemical name of this enzyme is β,D-fructofuranoside fructohydrolase. The enzyme is derived from baker's yeast (*Saccharomyces cerevisiae*), by enzymatic digestion with papain.

The Sucraid® product was typical of the era with respect to purity. The FDA established purity specification was not less than 85% in the main band(s) by reduced SDS-PAGE densitometry analysis following Coomassie staining. This is a band ratio of sacrosidase to other proteins of about 6:1.

The purity was specified by the FDA to comprise not more than 10 µg/mL of papain in the sacrosidase drug substance. The "drug substance" is the precursor glycerol:water solution of sacrosidase that can be further diluted and packaged to yield Sucraid®, which is referred to as the finished "drug product." The original label approved by FDA in 1998 made notice of potential for allergic reactions, and cautioned doctors to treat CSID patients for the first time within their unit in case allergic reactions arose. Again, in 2008, as the result of a site change of the drug substance manufacturer, the FDA only approved the re-launch of this drug with the imposition of a Risk Evaluation and Mitigation Strategy (REMS) which are only required by the FDA for drugs with the potential for serious safety problems.

It has been reported that the primary structure of sacrosidase consists of 513 amino acids with an apparent molecular weight of 100,000 g/mole for the glycosolated monomer (range 60,000-116,000 g/mole). Reports also suggest that the protein exists in solution as a monomer, dimer, tetramer, and octomer ranging from 100,000 g/mole to 800,000 g/mole. It has an isoelectric point of 4.1 (pI=4.093).

Presently, Sucraid® is provided in bottles containing 118 mL of the sacrosidase solution. A typical dose is either 1 or 2 mL with every meal or snack. The solution is bottled aseptically; however, it may become contaminated after opening due to the necessity of frequent administration, so patients are instructed to discard the bottle 4 weeks after opening.

SUMMARY OF THE INVENTION

This invention provides an ultrapure hypoallergic sacrosidase that meets the pharmaceutical standards for human prescription use. The sacrosidase is also organoleptically improved, since aqueous solutions thereof are odorless.

One embodiment provides a protein composition consisting of sacrosidase and containing no other proteins as determined by SDS-PAGE of up to about 15 µg of said composition. Techniques of SDS-PAGE, as described herein below, can employ reducing conditions and Coomassie Blue Staining. Thus, one embodiment provides a protein composition consisting essentially of sacrosidase having a band volume ratio of sacrosidase to other proteins of at least about 35:1, e.g., about 35-55:1, as determined by SDS-PAGE of about 20 µg of said composition. The protein composition of one embodiment is produced by a process comprising diafiltration of the yeast digest and does not employ chromatographic purification of said sacrosidase.

Another embodiment provides a drug substance and a drug product consisting essentially of a solution of sacrosidase in water comprising about 45-54 wt-% glycerol and that contains less than about 10 ng/mL, preferably less than about 3.0 ng/mL of papain in combination with at least about 7500 IU/mL of sacrosidase. One embodiment provides a solution consisting essentially of at least about 7500-9500 IU/mL, preferably about 8500 IU/mL sacrosidase in about 1:1 glycerol:water that contains less than about 3.0 ng/mL papain. This sacrosidase formulation does not induce an allergic reaction in a human subject such as a CSID patient, when administered at a dose of up to about 2.0 mL (daily doses of 2-10 mL).

Another embodiment provides a sacrosidase solution in water/glycerol having an activity of at least about 10,000 IU/mL and having less than about 10 ng/mL residual papain. In one embodiment, the solution has about a 1:1 wt-wt ratio of water to glycerol. In another embodiment, the solution has a pH of about 4.1-4.5.

The amount of papain can be determined by the techniques of ELISA. The solution is also not produced by a process comprising chromatographic purification of said sacrosidase.

As used herein the term "about" is intended to encompass variation in the referenced parameter, such as concentration, pH, enzymatic activity, time and the like that would be recognized by the art worker as necessarily inherent in determination of the parameter, e.g., see FIG. 1.

Additional information about Sucraid® and sacrosidase can be found in U.S. patent application Ser. No. 13/786,956, filed Mar. 6, 2013, which is incorporated by reference herein.

BRIEF DESCRIPTION OF THE FIGURES

FIG. 1 is a flow diagram of the current sacrosidase drug substance manufacturing process.

FIG. 5. The primary amino acid structure of Sacrosidase consists of 513 amino acids. Sacrosidase has the amino acid sequence shown below (SEQ ID NO:1).

DETAILED DESCRIPTION OF THE INVENTION

Figure 2:
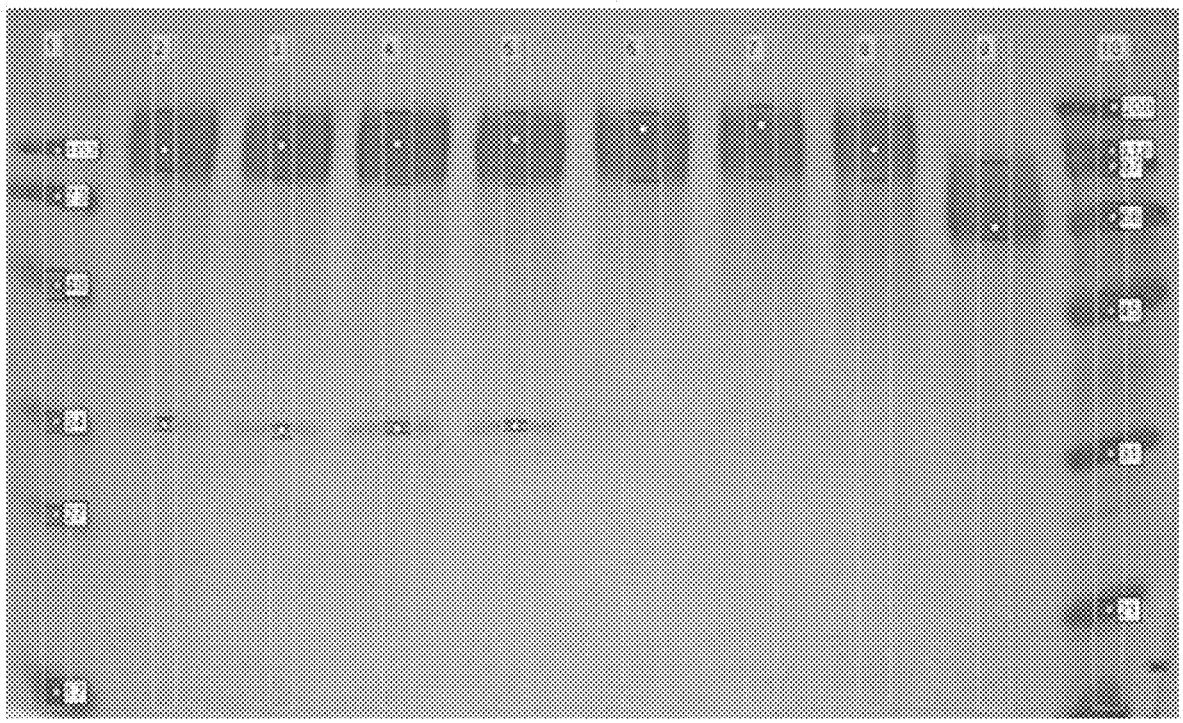
FIG. 2. Optimal Loaded SDS-PAGE gel Stained with Coomassie Blue. Sacrosidase bulk drug substance (FIG. 1) from two manufacturers (5 μg protein). Lane 1: Low range MW marker 17, 28, 34, 40, 73 and 102 kD; Lane 2: Reference Standard C4546; Lane 3: STS-199NS; Lane 4: STS-220NS; Lane 5: STS-241NS; Lane 6: 125275; Lane 7: 125434; Lane 8: 125722; Lane 9: Reference Standard C3955; Lane 10: Broad range MW marker (21, 34, 45, 66, 97 kD and 200 kD).

This invention provides an ultrapure hypoallergic sacrosidase that meets the pharmaceutical standards for human prescription use, with reduced allergenic properties. The sacrosidase is also organoleptically improved, since aqueous solutions thereof are odorless. Solutions of sacrosidase that are less pure can exhibit unpleasant organoleptic properties, such as a "yeasty" smell, unappetizing color and other odors.
Common Names: Invertase, Sacrosidase
Trade Name: Sucraid® (sacrosidase) oral solution (Drug Product)
USAN: Sacrosidase
Chemical: β-D-fructofuranoside fructohydrolase
Synonyms: β-D-fructofuranosidase
   β-D-fructofuranosidase
   β-fructofuranosidase
   β-fructofuranoside fructohydrolase
   β-fructopyranosidase
   β-fructosidase
   β-invertase
   Fructosylinvertase
   Invertase
   Invertin
   Glucosucrase
   Saccharase
   Sucrase
   Sucrose hydrolase
   Exo-β-(2,6)-Fructofuraosidase
   Maxivert L 1000
   Yeast Sucrase (YS)
CAS Number: 85897-35-4
   9001-57-4

Summary of the Purification Process

This invention provides a chromatography free process to produce ultrapure sacrosidase protein that meets pharmaceutical standards for human prescription use. Never before has a non-chromatographic method been developed to produce such ultra-high purity protein, particularly sacrosidase, overcoming prior shortcomings due to inadequate purity. A non-chromatographic purification process engenders significant cost and time savings during manufacturing. Provided herein is study drug characterization, purity evidence, and finally clinical proof of the improved unique hypoallergenic formulation.

The steps of a preferred embodiment of the present sacrosidase isolation and purification process are summarized in FIG. 1.

1. Digest yeast *saccharomyces* cerevisiae with papain in an aqueous buffered solution at a pH of about 7.0 and at a temperature of about 30-34° C.
2. The papain digestion cleaves all proteins into small molecular weight fragments that can later be effectively diafiltered away from the very large, papain resistant, sacrosidase enzyme, which in solution has an apparent native solution molecular weight of 500,000+ grains per mole (Daltons). Sacrosidase having the extensive glycosylation produced in yeast is resistant to papain digestion.
3. Use of diatomaceous earth with two different pore and/or particle sizes is preferred to remove most of the insoluble components, and likely other soluble and insoluble impurities. At the chosen pH, ionic strength, and concentrations, a large increase in purity occurs using these two steps in series that also prepares the resulting particulate free solution for diafiltration. Removal of insoluble components also prevents the dialysis membrane filters in the ultrafiltration unit from clogging. This increases the processing speed.
4. Diafiltration using an experimentally determined optimal pore size filter to balance purity with yield. The present process employs a minimum 40 kiloDalton cutoff filter to achieve an ultrapure hypoallergenic odorless solution of sacrosidase. The solution has a sacrosidase activity of at least about 22,000 IU/mL, preferably at least about 17,000 IU/mL. Larger pore filters give equivalent purity, but at the cost of yield. Smaller pore size filters do not provide sufficient final purity. Also experimentally determined was the number of batch volumes against which to diafilter: only 4+ diafiltration volumes allows for purity adequate to meet the requirements for a regulated bulk drug substance for human pharmaceutical use.
5. Final formulation of the drug substance with glycerol, preferably employs sterile filtration to ensure lot bioburden that meets FDA standards. The drug substance is stored in drums at about −18° C. to −25° C. for long term storage, until processed/concentration adjusted/packaged to yield the Sucraid® drug product. At this point, the sacrosidase activity is at least about 10,000 IU/mL.

The invention will be further described by reference to the following detailed examples, wherein the terms "SDS-PAGE" and "RASA" as used herein are defined with reference to the following techniques.

Polyacrylamide Gel Electrophoresis (SDS-PAGE) Analysis

Samples of the sacrosidase bulk drug substance containing predetermined amounts of total protein, were analyzed by Charles Rivers Laboratory, Malvern, Pa. and the assays were validated by Tekagen, Inc., Malvern, Pa.

Reducing SDS-PAGE (sodium dodecyl sulfate-polyacrylamide gel electrophoresis) is used to separate mixtures of polypeptides (in an electric field) into distinct bands. Mobility under these conditions is primarily determined by molecular size. Staining with Colloidal Coomassie Blue allows for visual and/or densitometric analysis of the resolved bands. This method is linear for loads from 0.25 µg to 15 µg with a lower limit of detection of 0.1 µg per band, e.g., the limits of detection and quantification of sacrosidase were determined to be 0.1 µg. The measured sacrosidase band area correlated linearly with the protein load.

In the assays herein below, the sacrosidase-containing samples described were reduced with 2-mercaptoethanol in SDS sample buffer. Samples were adjusted to about 1.0 mg/mL with water and treated with one volume of the mercaptoethanol in SDS buffer at 100® C. for 3 min. to denature/reduce the protein. Samples were run in an XCell SureLock Mini-Cell® (Invitrogen) using Novex® 4·20% Tris-Glycine Gel (Invitrogen) using an SDS running buffer for 90 min. at 120 volts. Gels were stained with Coomassie Blue and washed in water. Gels were scanned using a Personal Densitometer SI (Molecular Dynamics).

Papain Quantification by Enzyme-Linked Immunosorbent Assay (ELISA)

Samples of the sacrosidase bulk drug substance were dialyzed against PBS and any papain was inhibited with E-64. The sample was assayed for papain content by Warnex Laboratories, Quebec, Canada, using a quantitative sandwich-type ELISA. A polyclonal capture antibody (rabbit) specific to papain is coated in each well of a microplate. When present in the samples, papain binds to the capture antibody. A second anti-papain antibody (goat) conjugated with horse-radish peroxidase (HRP) is added which binds to any captured papain. After washing, the O-phenlenediamine substrate is added with 0.03% $H_2O_2$ to produce an enzymatic color reaction with HRP. The reaction is stopped with a solution of sulfuric acid (stopping solution). The color intensity formed by the enzymatic reaction is measured by spectrophotometry.

The quantity of papain in the samples was calculated based on a standard curve, where the average OD values of each of the standards are on the Y-axis and the corresponding concentration of papain is on the X-axis. To determine the final concentration of papain in the samples the concentration obtained from the standard curve is multiplied by the dilution factor. The quantity of papain is calculated automatically by the Gen5 software. The lower limit of quantification of papain is 3.13 ng/mL. The lower limit detection of papain is 1.56 ng/mL.

Example 1: Manufacturing Process for Ultrapure Sacrosidase

Deionized water (1700 kg) is charged to a 1000 gallon reactor and heated to 32±2° C. at which time *Saccharomyces cerevisiae* yeast (360 kg) is added and the slurry is mixed for 20-30 min. The pH is checked and if it is found to be below 6.9, the pH is adjusted using a 25% sodium hydroxide solution until the pH is 7.0±0.1.

Papain (3.4 kg) 100 TU/mg is added followed by hydrogen peroxide (35%, 2.8 kg). The slurry is stirred at 32±2° C. for the next 17.5 to 20 h; after every 3.5-4 h the pH is adjusted to 7.0±0.1 and hydrogen peroxide (34%, 2.8 kg each portion, 11.2 kg total) is added.

Once the 17.5-20 hours of mixing is complete the mixture is cooled to between 22° C. and 26° C. at which point 25 kg of 85% phosphoric acid is added over a 20-30 min period. The pH of the slurry is checked and the pH is further adjusted to 4.0±0.1 by addition of 85% phosphoric acid.

Diatomaceous earth (Celpure® S1000, 210 kg) is added to the mixture followed by an additional 700 kg of deionized water and the slurry is mixed for 30-40 min. The slurry is filtered in four equal portions through a sparkler filter to remove the cell debris and any other solids from the product in solution. For each portion of the filtration, once the filtrate collection rate stops the filter bundle is washed with fresh deionized water (400 kg). These washes are combined with the initial filtrates.

After the fourth filtration is complete the combined filtrates and washes are returned to the 1000-gallon reactor and treated with hydrogen peroxide (34%, 2.0 kg). The solution is decolorized by treatment with activated carbon (20×40 mesh, 60 kg) and aluminum sulfate (9.4 kg); the resulting slurry is mixed for 1.5-2 h.

Diatomaceous earth (Celpure® S100, 32 kg) is added and mixed for an additional 30 min. The solids are removed by filtration through the sparkler filter. The reactor is cleaned to remove any residual solids that may be present and the filtrate from decolorization is returned to the reactor through a 0.2-micron in-line filter. The solution is then concentrated to about 250 kg using an ultrafiltration unit that has been equipped with 40 kilo-Dalton cutoff filters.

The concentrated sacrosidase solution is then purified by diafiltration against at least four volumes (~1000 L) of citric acid buffer solution. This buffer solution is prepared from deionized water (1000 kg), citric acid (9.2 kg), sodium citrate (11.2 kg) and the pH of the solution is adjusted to 4.6±0.1 by addition of 25% sodium hydroxide. Additional volumes of buffer can be used to increase the overall protein purity while continuing to reduce residual levels of impurities in the final formulated solution. Typically four volumes (~1000 L) of citric acid buffer has been sufficient during diafiltration to purify the sacrosidase protein retained in the solution to >99% purity and to achieve papain levels <50 ppb.

Once the diafiltration is complete the solution is further concentrated until the material has an assay value ≥26,000 IU/mL in the sacrosidase assay test. The pH of the solution is then checked and adjusted to 4.3±0.1 by either use of 25% sodium hydroxide solution if the pH is <4.15 or by use of 85% phosphoric acid if the pH of the solution is >4.45.

Once the pH adjustment is complete the solution is transferred to a mixing vessel and an about equal weight of glycerin is added to produce the sacrosidase drug substance. The resulting water-glycerin solution is mixed for 10 min. The target drug substance has >10,000 IU/mL of sacrosidase and about 45-54 wt-% glycerol. Once the mixing is complete the solution is transferred to drums through two 0.2 micron nylon in-line filters that are set up in series. The drummed solution or "drug substance" is stored at room temperature for 8-36 h prior to being moved into long-term storage at about −20° C. Portions can be removed as needed and diluted and packaged to yield the Sucraid® drug product.

Example 2: Coomassie Blue Stained Reduced SDS-PAGE Gel with Densitometry—Optimal Load The gel shown in FIG. 2 is a Coomassie stained, reduced SDS-PAGE comparing 3 lots of a prior sacrosidase manufacturer (Lanes 3, 4, 5) that was manufactured with an older manufacturing process, with 3 lots of sacrosidase (Lanes 6, 7, 8) manufactured using the new ultra-pure hypoallergenic manufacturing process. Reference standard C4546 is the reference standard currently in use and was produced from the older process. Reference standard C3955 is an older-yet reference standard from the original Sacrosidase manufacturer.

The densitometry scan of this optimally loaded SDS-PAGE gel is shown below (Table 1). These results clearly show that the sacrosidase manufactured using the new process is ultrapure with no detectable protein impurities. The cGMP validation of this method established a limit of detection of less than 0.1 micrograms.

TABLE 1

| Sample Type | Lot Number | Lane No. | Band No. | Band Volume | % Density |
|---|---|---|---|---|---|
| Reference Standard | C4546 | 2. | 1. | 1823 | 94.31 |
| | | 2. | 2. | 110 | 5.69 |
| Old Process | STS-199NS | 3. | 1. | 2376 | 94.93 |
| | | 3. | 2. | 127 | 5.07 |
| Old Process | STS-220NS | 4. | 1. | 2822 | 94.83 |
| | | 4. | 2. | 154 | 5.17 |
| Old Process | STS-241NS | 5. | 1. | 2590 | 94.46 |
| | | 5. | 2. | 152 | 5.54 |
| New Process | 125275 | 6. | 1. | 2356 | >99.9 |
| New Process | 125434 | 7. | 1. | 2331 | >99.9 |
| New Process | 125722 | 8. | 1. | 2159 | >99.9 |
| Reference Standard* | C3955 | 9. | 1. | 2256 | >99.9 |

*Purified by chromatography. Experimental sample only.

Figure 3:
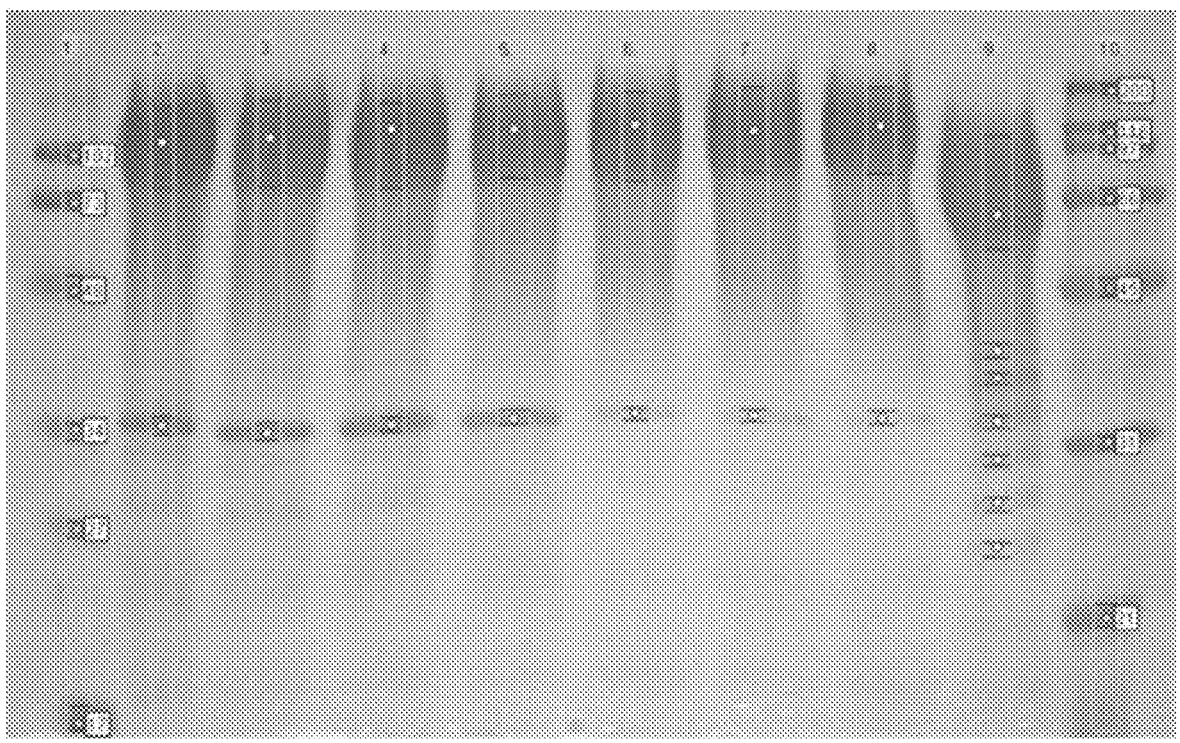
FIG. 3. Overloaded SDS-PAGE gel Stained with Coomassie. Sacrosidase bulk drug substance from two manufacturers (20 μg protein). Lane 1: Low range MW marker; Lane 2: Reference Standard C4546; Lane 3: STS-199NS; Lane 4: STS-220NS; Lane 5: STS-241NS; Lane 6: 125275; Lane 7: 125434; Lane 8: 125722; Lane 9: Reference Standard 03955; Lane 10: Broad range MW marker.

Example 3: Coomassie Stained Reduced SDS-PAGE Gel with Densitometry—Overloaded Gel In a second protocol reduced SDS-PAGE gels were overloaded with 20 μg of protein (FIG. 3). In the Coomassie stained gels, a small impurity band is visible in the present sacrosidase drug substance, but the absolute purity of the sacrosidase of the invention (~97%, Lanes 6, 7, 8) is still superior to the older sacrosidase (~90%, Lanes 3, 4, 5). Table 2 summarizes the information from this gel.

TABLE 2

| Sample Type | Sample Lot | Protein Qty (μg) | Lane No. | Band No. | Band rf | Band Volume | Band Sum | % Density |
|---|---|---|---|---|---|---|---|---|
| Reference Standard | C4546 | 20 | 2. | 1. | 0.151 | 4419 | 4867 | 90.80 |
| | | | 2. | 2. | 0.561 | 448 | | 9.20 |
| Old Process | STS-199NS | 20 | 3. | 1. | 0.145 | 5063 | 5588 | 90.60 |
| | | | 3. | 2. | 0.568 | 525 | | 9.40 |
| Old Process | STS-220NS | 20 | 4. | 1. | 0.132 | 5460 | 5969 | 91.47 |
| | | | 4. | 2. | 0.559 | 509 | | 8.53 |
| Old Process | STS-241NS | 15 | 5. | 1. | 0.132 | 4577 | 5003 | 91.49 |
| | | | 5. | 2. | 0.550 | 426 | | 8.51 |
| New Process | 125275 | 15 | 6. | 1. | 0.126 | 5157 | 5292 | 97.45 |
| | | | 6. | 2. | 0.542 | 135 | | 2.55 |
| New Process | 125434 | 15 | 7. | 1. | 0.134 | 4820 | 4936 | 97.65 |
| | | | 7. | 2. | 0.546 | 116 | | 2.35 |
| New Process | 125722 | 15 | 8. | 1. | 0.128 | 4832 | 4931 | 97.99 |
| | | | 8. | 2. | 0.550 | 99 | | 2.01 |
| Reference Standard | C3955 | 15 | 9. | 1. | 0.257 | 5640 | 6326 | 89.16 |
| | | | 9. | 2. | 0.450 | 69 | | 1.09 |
| | | | 9. | 3. | 0.490 | 135 | | 2.13 |
| | | | 9. | 4. | 0.554 | 108 | | 1.71 |
| | | | 9. | 5. | 0.609 | 96 | | 1.52 |
| | | | 9. | 6. | 0.669 | 143 | | 2.26 |
| | | | 9. | 7. | 0.732 | 135 | | 2.13 |

Example 4: Optimal and Overloaded Native Gels

In a third protocol non-reduced samples were run on native PAGE gels. Both optimal (5 µg protein) and overloaded (20, 30 & 60 µg protein) protein were applied to polyacrylamide gels then stained with Coomassie Blue.

Figure 4:
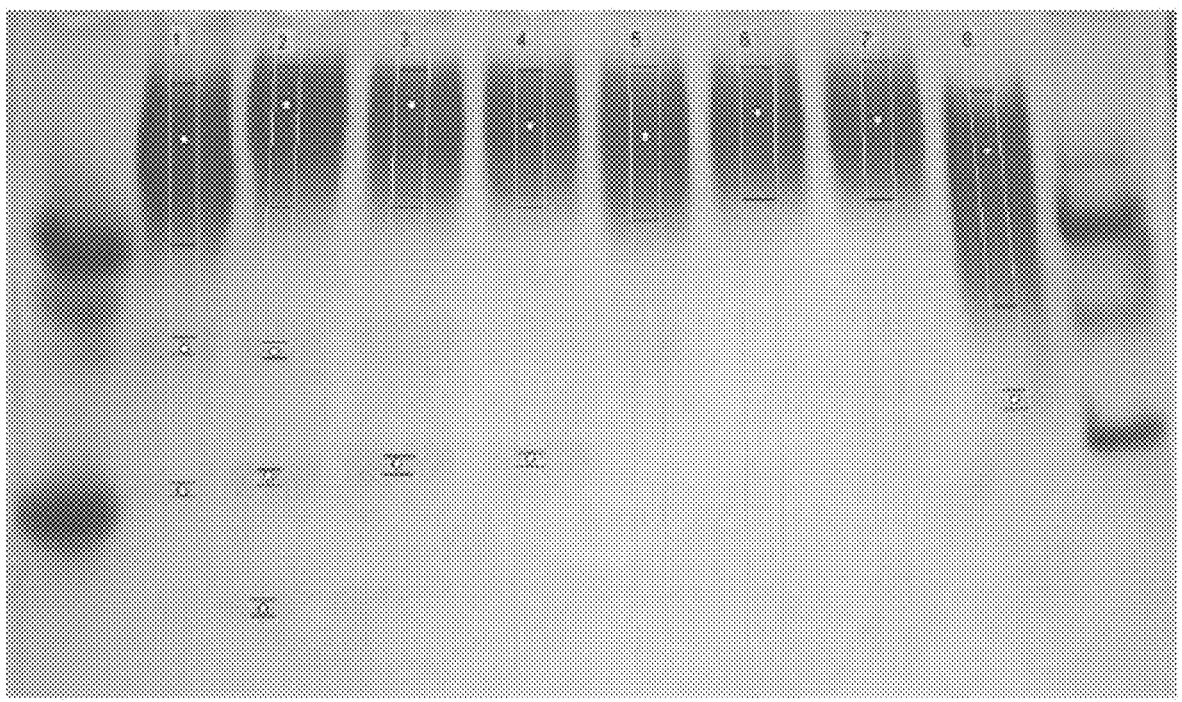
FIG. 4. Overloaded Native gel stained with Coomassie. Sacrosidase bulk drug substance from two manufacturers (15 μg protein). Lane 1: Reference Standard C4546; Lane 2: STS-199NS; Lane 3: STS-220NS; Lane 4: STS-241NS; Lane 5: 125275; Lane 6: 125434; Lane 7: 125722; Lane 8: Reference Standard C3955.

FIG. 4 depicts an overloaded (15 µg) Coomassie stained native gel. Densitometry scanning of the gel show purity values of 97.59, 99.02, and 99.31 for sacrosidase made by the older sacrosidase process and 100%, 100% and 100% for the sacrosidase manufactured using the present ultrapure process. This gel clearly demonstrates the ultrapure quality of the sacrosidase manufactured using the new process. Table 3 summarizes the information from this gel.

TABLE 3

| Sample Type | Sample Lot | Protein Qty (µg) | Lane No. | Band No. | Band rf | Band Volume | Band Sum | % Density |
|---|---|---|---|---|---|---|---|---|
| Reference | C4546 | 15 | 1. | 1. | 0.170 | 10034 | 10167 | 98.69 |
|  |  |  | 1. | 2. | 0.492 | 62 |  | 0.61 |
|  |  |  | 1. | 3. | 0.711 | 71 |  | 0.70 |
| Old Process | STS-199NS | 15 | 2. | 1. | 0.115 | 8926 | 9146 | 97.59 |
|  |  |  | 2. | 2. | 0.495 | 51 |  | 0.56 |
|  |  |  | 2. | 3. | 0.689 | 86 |  | 0.94 |
|  |  |  | 2. | 4. | 0.896 | 83 |  | 0.91 |
| Old Process | STS-220NS | 15 | 3. | 1. | 0.120 | 8473 | 8557 | 99.02 |
|  |  |  | 3. | 2. | 0.679 | 84 |  | 0.98 |
| Old Process | STS-241NS | 15 | 4. | 1. | 0.150 | 8670 | 8730 | 99.31 |
|  |  |  | 4. | 2. | 0.662 | 60 |  | 0.69 |
| New Process | 125275 | 15 | 5. | 1. | 0.166 | 9100 | 9100 | 100 |
| New Process | 125434 | 15 | 6. | 1. | 0.129 | 7967 | 7967 | 100 |
| New Process | 125722 | 15 | 7. | 1. | 0.141 | 8605 | 8605 | 100 |
| Reference | C3955 | 15 | 8. | 1. | 0.190 | 13693 | 13744 | 99.63 |
|  |  |  | 8. | 2. | 0.573 | 51 |  | 0.37 |

Example 5: Three Order of Magnitude (1,000 Fold) Reduction in a Protein Impurity The FDA recalled all topical papain products in 2008 due to risk of hypersensitivity reactions (www.fda.gov/NewsEvents/Newsroom/PressAnnouncements/2008/ucm116956.htm) and a REMS was required for sacrosidase that same year (www.fda.gov/downloads/Drugs/DrugSafety/PostmarketDrugSafetyInformationforPatientsandProviders/UCM144251.pdf). The present process demonstrates an impressive three order of magnitude reduction in the papain levels of the drug substance to nearly undetectable levels with a very sensitive ELISA (LOQ of 3 ng/mL) using this new chromatography-free process. LOQ is the limit of quantitation. These lots below were the end result of three process validation lots from the present process (Lots 125275, 125897, 125907) versus the old manufacturer lots (STS-199NS, STS-220NS, STS-241NS) which carried an FDA imposed papain limit of 10,000 ng/mL.

TABLE 4

Sacrosidase lot number with papain concentration underneath in ng/mL

| STS-199NS | STS-220NS | STS-241NS | 125275 | 125897 | 125907 |
|---|---|---|---|---|---|
| 7300 | 8050 | 5470 | <3 | <3 | <3 |

This example shows the substantial level of reduction of papain to undetectable levels. Papain at 23 kilo-Daltons is a key marker protein that is likely representative of any other proteins below the 40 KD cutoff limit of the ultrafiltration filter used, along with the proteins cleaved by papain that fall above the 40 KD molecular weight cut-off, with the exception of sacrosidase which is resistant to papain cleavage in its three dimensional native form in solution.

Example 6: Organoleptic Properties Improved

While diafiltering the solution after concentration, an operator was tasked with observing the color and smell of the concentrated sacrosidase solution. As the number of wash volumes increased from no (zero) diafiltration wash volumes up to four (4) diafiltration wash volumes, the operator observed that all yeast smell was removed from the sacrosidase solution and the yellow color was dramatically reduced to almost no yellow color. These organoleptic properties of this new ultrapure formulation are important for young pediatric patient compliance as the "yeasty smell" is not tolerated well by some young patients leading to poor compliance with their prescribed Sucraid dosing.

Example 7: Clinical Evidence of Improved Safety and Continued Efficacy

A 5 year old female CSID patient was first dosed with the old formulation of Sucraid in August 2012, and as instructed by the FDA approved labeling (package insert) due to the possibility of allergic reactions, she was dosed the first time within her physicians' offices. This patient manifested a whole body case of hives immediately after dosing with the old formulation of Sucraid. Further dosing with Sucraid was therefore precluded. The family was eager to find a solution to their daughters gastrointestinal problems, so acceded to a second challenge with different lot of the old formulation of Sucraid about 2 months later. Again, hives manifested, and so this patient was permanently precluded from using the commercially marketed FDA approved Sucraid to treat her genetically determined sucrase deficiency.

After this new ultrapure hypoallergenic formulation of sacrosidase was developed, an IND was filed and authorized by FDA, along with Institutional Review Board (IRB) approval at the Mayo Clinic in Rochester Minn. for a test dosing protocol in this same patient in November 2013.

After treatment with the new ultrapure hypoallergenic formulation of sacrosidase, this 5 year old patient no longer manifested allergic reactions or symptoms, including hives. Further, after taking the new ultrapure hypoallergenic formulation of Sucraid her CSID symptoms were completely ameliorated, including normalizing to 1-2 formed stools per day versus >6+ watery diarrhea type bowel movements per day, elimination of her abdominal pain, and elimination of her abdominal distension, so that this pediatric patient is now able to utilize this life changing medication to treat her disease. The new ultrapure hypoallergenic formulation of sacrosidase is being provided to this patient for chronic use pursuant to an FDA approved IND along with Mayo IRB approval with excellent results for control of her CSID disease.

What is claimed is:

1. A method for treating a subject who lacks endogenous sucrase activity, comprising orally administering an effective amount of a protein composition consisting essentially sacrosidase having a band volume ratio of sacrosidase to other proteins comprising papain of at least about 35:1 by SDS-PAGE of about 20 μg of said composition, wherein the primary structure of the sacrosidase is a 513 amino acid polypeptide that is gycosylated.

2. The method of claim 1 wherein the band volume ratio is about 35-55:1.

3. A method of treating a subject who lacks endogenous sucrase activity comprising orally administering an effective amount of a protein composition consisting essentially of sacrosidase derived from *Saccharomyces* having residual papain in a concentration of less than about 10 ng/mL, papain, and having a band volume ratio of sacrosidase to other proteins comprising papain of at least about 35:1 by SDS-PAGE of about 20 μg of said composition, wherein the primary structure of the sacrosidase is a 513 amino acid polypeptide that is glycosylated.

4. The method of claim 3 wherein the protein composition is administered in a solution.

5. The method of claim 4 wherein the sacrosidase has an enzyme activity of at least about 7500 IU/ml.

6. The method of claim 4 wherein a daily dose of the solution of about 2-10 mL per day does not induce an allergic reaction in a human patient afflicted with congenital sucrase-isomaltase deficiency.

7. The method of claim 3 wherein the sacrosidase contains less than about 3.0 ng/mL papain.

8. The method of claim 3 wherein the sacrosidase contains no detectable papain by an enzyme-linked immunosorbant assay having a lower limit of quantification of 3 ng/mL.

9. The method of claim 4 wherein the solution of sacrosidase contains no detectable papain by SDS-PAGE of up to about 15 μg of said solution.

10. The method of claim 5 wherein the solution of sacrosidase has enzymatic activity of about 7500-10,000 IU/ml.

* * * * *